(12) United States Patent
Shaw et al.

(10) Patent No.: US 8,217,011 B2
(45) Date of Patent: Jul. 10, 2012

(54) PEPTIDES, COMPOSITIONS AND USES THEREOF

(75) Inventors: Christopher Shaw, Belfast (GB); Tianbao Chen, Belfast (GB); Martin O'Rourke, Belfast (GB); Brian Walker, Belfast (GB); David Hirst, Belfast (GB)

(73) Assignee: The Queen's University of Belfast, Belfast (GB)

( * ) Notice: Subject to any disclaimer, the term of this patent is extended or adjusted under 35 U.S.C. 154(b) by 0 days.

(21) Appl. No.: 12/449,950

(22) PCT Filed: Mar. 7, 2008

(86) PCT No.: PCT/GB2008/050163
§ 371 (c)(1),
(2), (4) Date: Jun. 11, 2010

(87) PCT Pub. No.: WO2008/107722
PCT Pub. Date: Sep. 12, 2008

(65) Prior Publication Data
US 2010/0249035 A1 Sep. 30, 2010

(30) Foreign Application Priority Data
Mar. 7, 2007 (GB) .................................. 0704352.4

(51) Int. Cl.
*A61K 38/08* (2006.01)
*A61L 15/16* (2006.01)
*C07K 7/06* (2006.01)

(52) U.S. Cl. ..................... 514/21.8; 530/329; 424/447

(58) Field of Classification Search ........................ None
See application file for complete search history.

(56) References Cited

FOREIGN PATENT DOCUMENTS
| WO | WO 2004/068928 | | 8/2004 |
| WO | WO 2004/069857 | | 8/2004 |
| WO | WO 2007/023396 | * | 3/2007 |

OTHER PUBLICATIONS

Chen, et al. "Kinestatin: a novel bradykinin $B_2$ receptor antagonist peptide from the skin secretion of the Chinese toad, *Bombina maxima*", *Regulatory Peptides* 116 (2003) 147-154.
Guo, et al., "Two faces of high-molecular-weight kininogen (HK) in angiogenesis: bradykinin turns it on and cleaved HK (HKa) turns it off", *Journal of Thrombosis and Haemostasis*, 3: 670-676 (2005).
Lee, et al. "Cloning of bradykinin precursor cDNAs from skin of *Bombina maxima* reveals novel bombinakinin M antagonists and a bradykinin potential peptide", *Regulatory Peptides* 127 (2005) 207-215.
Sun, et al., "Fibrosis of atria and great vessels in response to angiotensin II or aldosterone infusion", *Cardiovascular Research* 35 (1997) 138-147.

* cited by examiner

*Primary Examiner* — Marianne P Allen
(74) *Attorney, Agent, or Firm* — Drinker Biddle & Reath LLP

(57) ABSTRACT

Described is an N-terminal hexapeptide fragment of maximakinin, QUB 698.8, which exhibits potent tissue selective actions on smooth muscle. It demonstrates a high degree of selectivity for arterial smooth muscle over small intestinal smooth muscle, causing potent relaxation of arterial smooth muscle, while causing less potent contraction of ileal smooth muscle. It may be used treatment of diseases of the cardiovascular system and in promotion of angiogenesis.

3 Claims, 4 Drawing Sheets

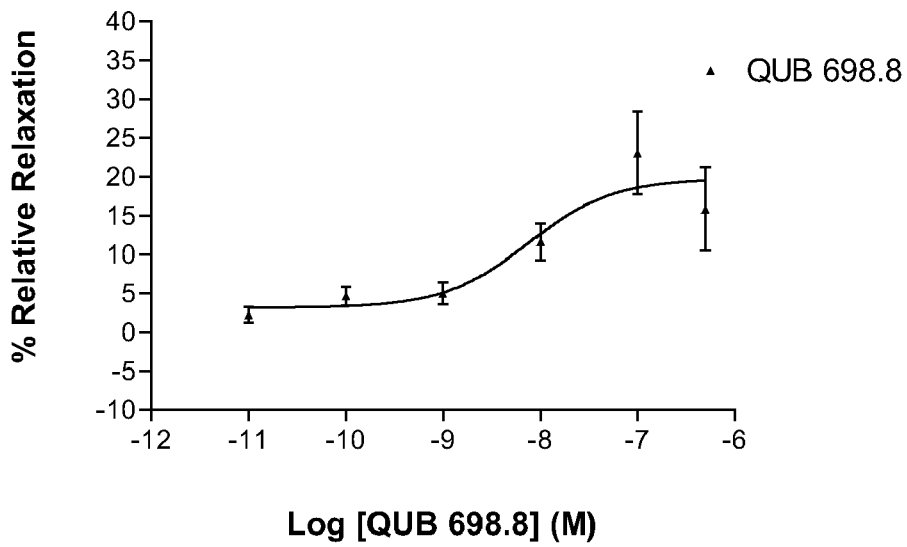
Figure 1a: The effect of QUB 698.8 in phenylephrine pre-constricted rat tail artery
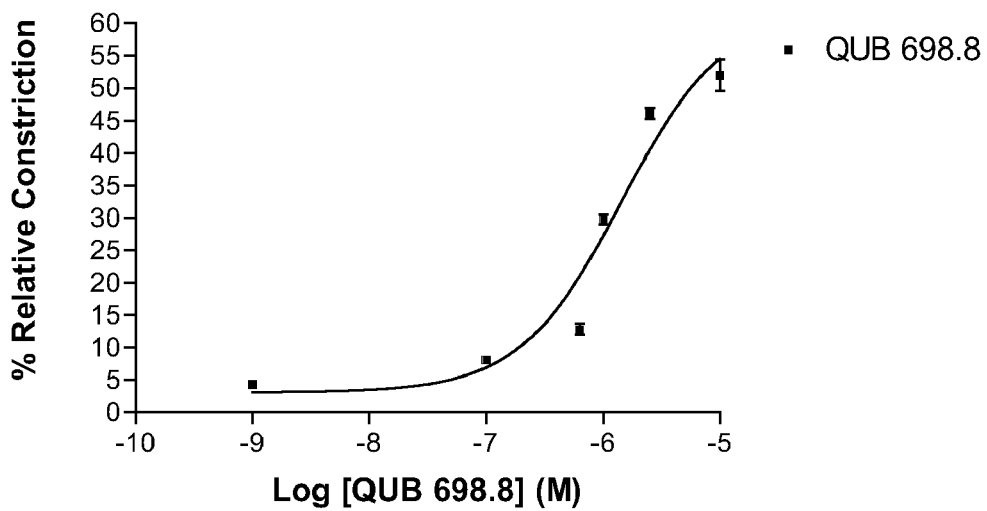
Figure 1b: Effect of QUB 698.8 on spontaneously contracting ileum rings

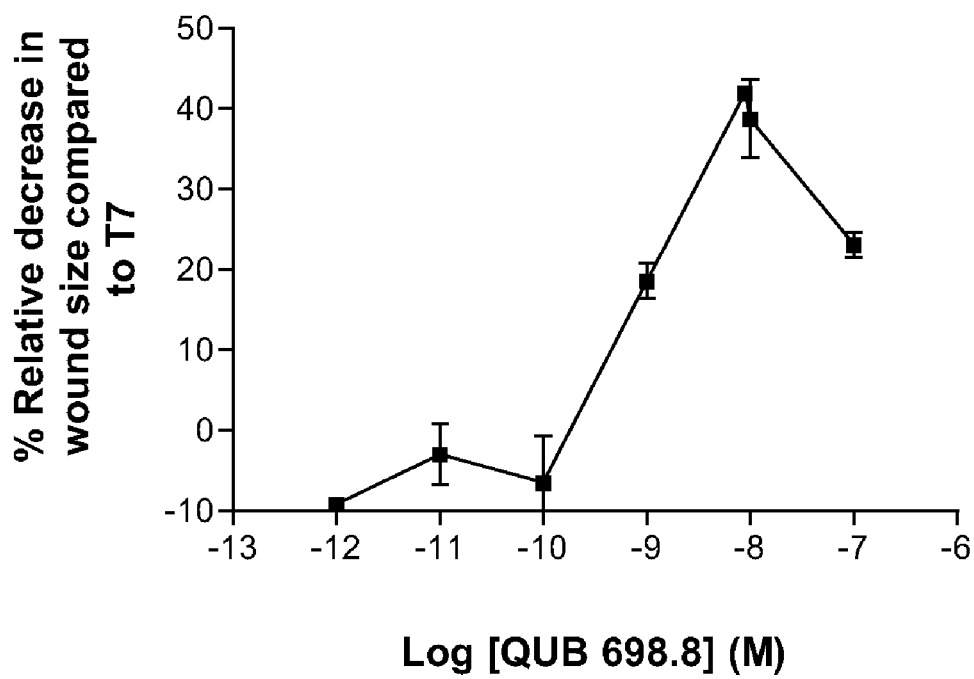
Figure 2a: Effect of QUB 698.6 on the migration of HMEC-1 in the wound scrape assay

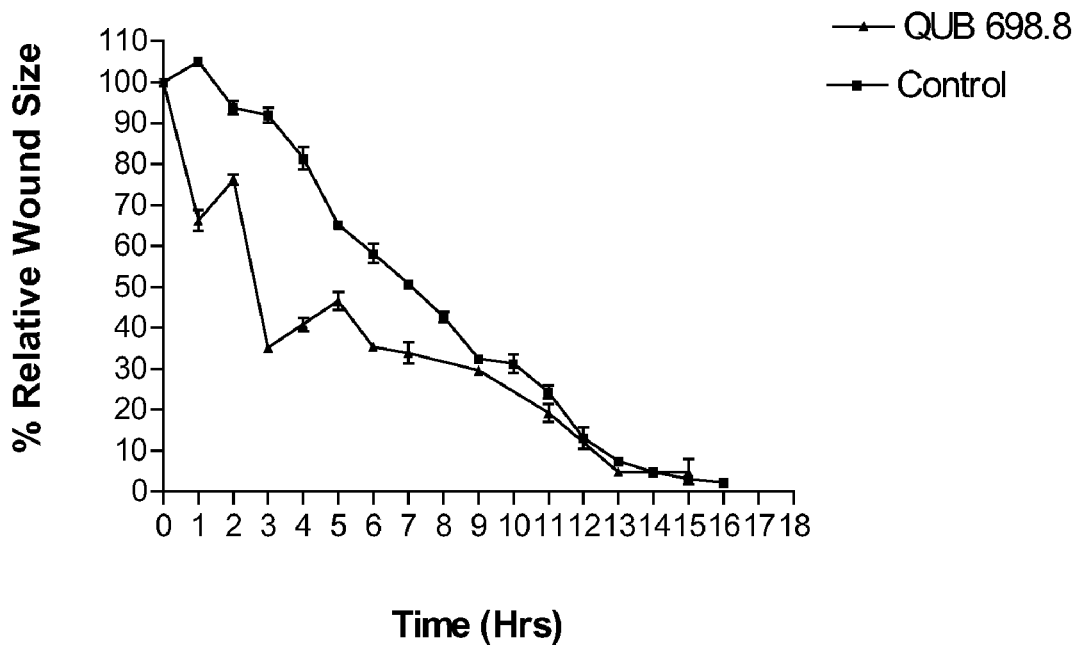
Figure 2b: The effect of QUB 698.8 ($10^{-8}$M) on the time dependent migration of HMEC-1 in the wound assay
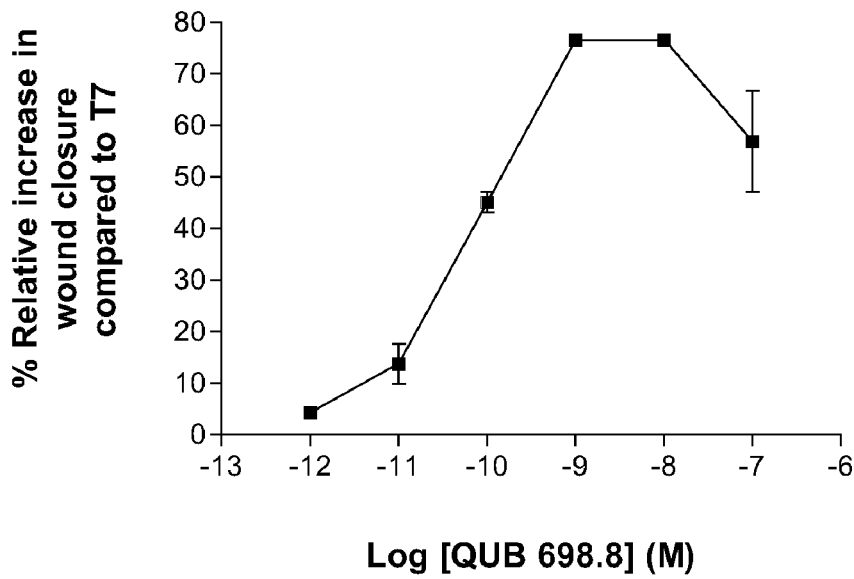
Figure 3: Effect of QUB 698.8 on the ability of HMEC-1 to form tubules on Matrigel Matrices

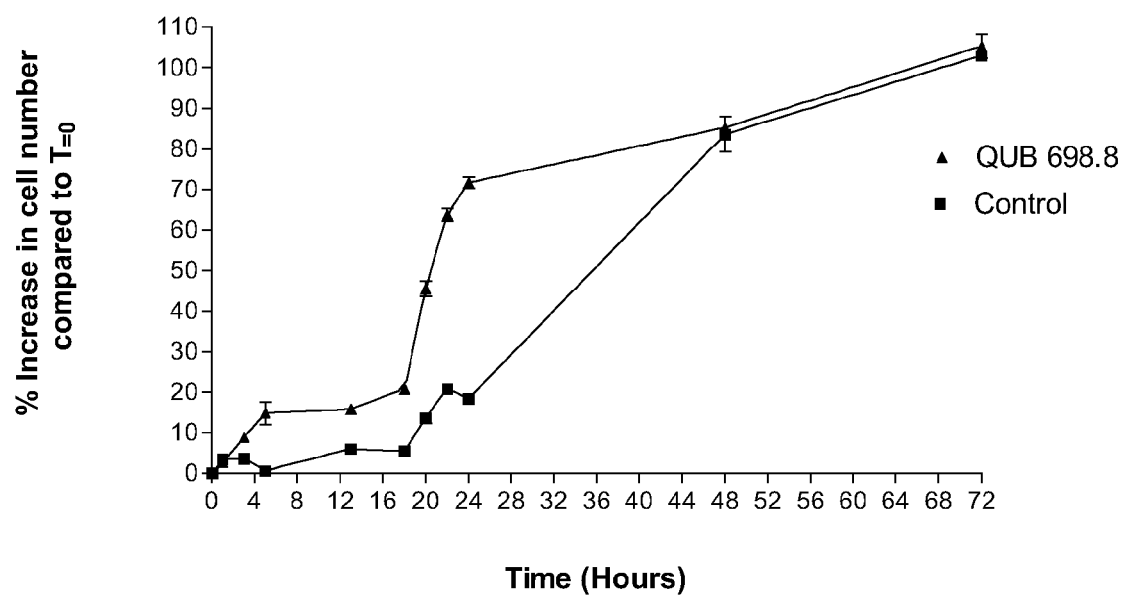
Figure 4: The effect of QUB698.8 on the proliferation of HMEC-1 over 72 hours

SEQUENCE LISTING

<160> NUMBER OF SEQ ID NOS: 10

<210> SEQ ID NO 1
<211> LENGTH: 19
<212> TYPE: PRT
<213> ORGANISM: Bombina maxima

<400> SEQUENCE: 1

Asp Leu Pro Lys Ile Asn Arg Lys Gly Pro Arg Pro Pro Gly Phe Ser
1               5                   10                  15

Pro Phe Arg

<210> SEQ ID NO 2
<211> LENGTH: 6
<212> TYPE: PRT
<213> ORGANISM: Bombina maxima

<400> SEQUENCE: 2

Asp Leu Pro Lys Ile Asn
1               5

<210> SEQ ID NO 3
<211> LENGTH: 5
<212> TYPE: PRT
<213> ORGANISM: Bombina maxima

<400> SEQUENCE: 3

Leu Pro Lys Ile Asn
1               5

<210> SEQ ID NO 4
<211> LENGTH: 5
<212> TYPE: PRT
<213> ORGANISM: Bombina maxima

<400> SEQUENCE: 4

Asp Leu Pro Lys Ile
1               5

<210> SEQ ID NO 5
<211> LENGTH: 8

```
<212> TYPE: PRT
<213> ORGANISM: Bombina maxima

<400> SEQUENCE: 5

Asp Leu Pro Lys Ile Asn Arg Lys
1               5

<210> SEQ ID NO 6
<211> LENGTH: 8
<212> TYPE: PRT
<213> ORGANISM: Bombina maxima

<400> SEQUENCE: 6

Leu Pro Lys Ile Asn Arg Lys Gly
1               5

<210> SEQ ID NO 7
<211> LENGTH: 9
<212> TYPE: PRT
<213> ORGANISM: Bombina maxima

<400> SEQUENCE: 7

Asp Leu Pro Lys Ile Asn Arg Lys Gly
1               5

<210> SEQ ID NO 8
<211> LENGTH: 9
<212> TYPE: PRT
<213> ORGANISM: Bombina maxima

<400> SEQUENCE: 8

Leu Pro Lys Ile Asn Arg Lys Gly Pro
1               5

<210> SEQ ID NO 9
<211> LENGTH: 6
<212> TYPE: PRT
<213> ORGANISM: Bombina maxima

<400> SEQUENCE: 9

Asn Ile Lys Pro Leu Asp
1               5

<210> SEQ ID NO 10
<211> LENGTH: 18
<212> TYPE: DNA
<213> ORGANISM: Bombina maxima

<400> SEQUENCE: 10
gatttgccta agatcaac                                                 18
```

PEPTIDES, COMPOSITIONS AND USES THEREOF

FIELD OF THE INVENTION

The present invention relates to peptides, compositions and uses thereof. In particular it relates to peptides, which are based on the N-terminal hexapeptide of maximakinin (syn. bombinakinin M) and which have cell growth stimulatory activity, particularly in promoting angiogenesis, and uses thereof in methods of therapy.

INTRODUCTION

The defensive secretions from the dermal granular or poison glands of amphibians, particularly those of anurans, are complex molecular cocktails containing proteins, biogenic amines, alkaloids and a plethora of bioactive peptides (Lazarus, L. H. and Atilla, M. (1993) Prog. Neurobiol. 41, 473-507). Many skin peptides exhibit high degrees of structural similarity with endogenous vertebrate regulatory peptides but are usually more bioactive as a consequence of structural modifications occurring outside the conserved bioactive core sequence, an attribute produced by their natural selection for an exogenous delivery mode (Erspamer et al (1985) Peptides 6, Suppl. 3, 7-12). Caerulein, bombesin, dermorphin and deltorphin are examples of amphibian skin peptides that display enhanced activity at endogenous vertebrate cholecystokinin (CCK), gastrin-releasing peptide (GRP) and µ- and δ opioid receptors, respectively (Anastasi et al (1971) Experientia 27, 166-167; Anastasi et al (1968) Archs. Biochem. Biophys. 125, 57-68; Broccardo et al (1981) Br. J. Pharmacol. 73, 625-631; Kreil et al (1989) Eur. J. Pharmacol. 162, 123-128 10).

A number of bradykinin-like peptides have been isolated from amphibian skin secretions, some of which are believed to be associated with defence mechanisms of the Amphibia (Conlon and Aronsson (1997) Peptides 18, 361-365; Yasuhara et al (1979) Chem. Pharm. Bull. (Tokyo) 27, 486-491; Nakajima, T. (1968) Chem. Pharm. Bull. (Tokyo) 16, 769-774; Anastasi et al (1966) Br. J. Pharmacol. 27, 479-485; Yasuhara et al (1973) Chem. Pharm. Bull. (Tokyo) 21, 138-139). Lai et al (2001) Biochem. Biophys. Res. Commun. 286, 259-263 described the isolation of a bradykinin related peptide from the skin secretions of the toad Bombina maxima. Although this peptide, named bombinakinin M, was found to have contractile activity on guinea pig ileum smooth muscle, the authors of this paper suggest that the physiological role of the peptide is unclear.

In WO 2004/069857, which shares the principal inventor with the present application, an N-terminally extended bradykinin, maximakinin, is described. Maximakinin has amino acid sequence: Asp-Leu-Pro-Lys-Ile-Asn-Arg-Lys-Gly-Pro-Arg-Pro-Pro-Gly-Phe-Ser-Pro-Phe-Arg (SEQ ID NO: 1). Maximakinin, which has the same amino acid sequence as bombinakinin M (Lai et al (2001) Biochem. Biophys. Res. Commun. 286, 259-263) was found to demonstrate tissue selectivity in its actions on smooth muscle. Also identified in WO 2004/069857 were a number of C-terminal active fragments of maximakinin.

SUMMARY OF THE INVENTION

The present inventors have studied N-terminal fragments of maximakinin and have surprisingly demonstrated that, contrary to expectations, an N-terminal fragment of maximakinin, exhibits potent tissue selective actions on smooth muscle. Specifically, it was found that, despite the absence of the C-terminal residues of maximakinin, which were previously thought to be necessary for its activity, an N-terminal hexapeptide herein referred to as QUB 698.8, demonstrates a high degree of selectivity for arterial smooth muscle over small intestinal smooth muscle, causing potent relaxation of arterial smooth muscle, while causing less potent contraction of ileal smooth muscle.

Moreover, not only does such an N-terminal fragment retain the tissue selective properties of maximakinin, but it is significantly more potent than maximakinin.

Furthermore, the inventors unexpectedly found that, despite the previous studies involving maximakinin suggesting that the pro-angiogenic effects of this molecule and fragments thereof were also dependent on the presence of C-terminal residues of maximakinin, the N-terminal hexapeptide QUB698.8 demonstrates potent pro-angiogenic activity.

Accordingly, in a first aspect, the present invention provides a pro-angiogenic peptide, wherein said pro-angiogenic peptide is QUB698.8 or a biologically active fragment or derivative thereof.

QUB698.8 has the amino acid sequence:

Asp-Leu-Pro-Lys-Ile-Asn    (SEQ ID NO: 2)

In one embodiment the pro-angiogenic peptide of the invention consists of the amino acid sequence Asp-Leu-Pro-Lys-Ile-Asn    (SEQ ID NO: 2)

In the context of the present invention, a fragment of QUB698.8 is a peptide having at least five contiguous amino acids corresponding to a segment of QUB698.8 having the same five contiguous amino acids.

Derivatives of QUB698.8 include peptides having the amino acid sequence of SEQ ID NO: 2 with one, two, or three amino acid substitutions, insertions, deletions, or a combination thereof.

In one embodiment, the derivative comprises at least five contiguous amino acids of QUB 698.8.

Specific derivatives include:

| | |
|---|---|
| Leu-Pro-Lys-Ile-Asn | (SEQ ID NO: 3) |
| Asp-Leu-Pro-Lys-Ile | (SEQ ID NO: 4) |
| Asp-Leu-Pro-Lys-Ile-Asn-Arg-Lys | (SEQ ID NO: 5) |
| Leu-Pro-Lys-Ile-Asn-Arg-Lys-Gly | (SEQ ID NO: 6) |
| Asp-Leu-Pro-Lys-Ile-Asn-Arg-Lys-Gly | (SEQ ID NO: 7) |
| Leu-Pro-Lys-Ile-Asn-Arg-Lys-Gly-Pro. | (SEQ ID NO: 8) |

Furthermore, derivatives may comprise additional amino acids at the N- and/or C-terminal. In such embodiments, the derivative preferably comprises one to eleven additional amino acids for example, two, three, four, five, six, seven, eight, nine, ten or eleven amino acids. In the context of the present application, such derivatives do not include a peptide having the amino acid sequence of maximakinin itself.

Such fragments and derivatives preferably retain pro-angiogenic activity.

Unless the context demands otherwise, reference to peptides of the invention encompasses such derivatives and fragments.

According to a second aspect of the present invention there is provided a polynucleotide encoding a peptide according to the first aspect of the invention, wherein said polynucleotide does not encode a polypeptide comprising an amino acid sequence shown as Sequence ID No: 1.

According to a third aspect of the present invention there is provided a method of inducing relaxation of arterial smooth muscle cells or tissue, said method comprising administering a pro-angiogenic peptide of the first aspect of the invention, or a polynucleotide according to the second aspect of the invention to said cell or tissue.

In one embodiment of the invention, the EC50 of the pro-angiogenic peptide of or for use in the invention at arterial smooth muscle is less than the EC50 of maximakinin at arterial smooth muscle cells, and/or the EC50 of the pro-angiogenic peptide of the invention at small intestinal cells is more than the EC50 of maximakinin at small intestinal cells.

The surprising demonstration that the peptides of the invention exhibit such potent, yet selective effects on smooth muscle receptors, enables the use of such peptides in the treatment of diseases of the cardiovascular system while minimising side effects associated with the use of less selective agents.

Accordingly, in a fifth aspect of the present invention, there is provided a method of promoting vasodilation in a tissue, comprising administering a peptide according to the first aspect of the invention or a polynucleotide according to the second aspect of the invention, to said tissue.

The peptides, polynucleotides and methods of the invention may be particularly useful in the treatment of cardiovascular disease while minimising unwanted side effects, for example on the gastrointestinal system.

Accordingly, in a sixth aspect of the invention, there is provided a method of treating a cardiovascular disease, said method comprising administering a therapeutically effective amount of a peptide of the first aspect of the invention or a polynucleotide according to the second aspect of the invention to a patient in need thereof.

Cardiovascular diseases for which the present invention may be used include any cardiovascular disease, condition or symptom for which vasodilation may be useful. For example, in one embodiment, the cardiovascular disease is hypertension. In another embodiment, the cardiovascular disease is pulmonary hypertension. In a further embodiment, the cardiovascular disease is coronary artery disease. In a further embodiment, the cardiovascular disease is peripheral vascular disease. In a further embodiment, the cardiovascular disease is an ischemic condition, for example angina or and stroke. Other diseases for which the peptides and methods of the invention may be used include the treatment of vasospasm, for example, intra- or post-operatively, and erectile dysfunction.

The invention may be used to treat acute conditions where acute vasodilation may be beneficial.

As described above, the inventors have also surprisingly shown that the peptides of the invention demonstrate potent pro-angiogenic effects. Thus the data disclosed herewith is indicative of a potent role for the peptides of the invention in promoting the growth of new blood vessels.

Thus according to a seventh aspect of the present invention there is provided the use of a pro-angiogenic peptide according to the first aspect of the invention or a polynucleotide according to the second aspect of the invention in promoting angiogenesis in a biological sample.

In the context of the present invention, references to promoting angiogenesis should be understood to refer to inducing or accelerating an angiogenic taxic response or the inducing or accelerating of angiogenesis per se i.e. vessel formation.

According to an eighth aspect of the present invention there is provided a method of stimulating angiogenic taxic responses in cells comprising administering a pro-angiogenic peptide according to the first aspect of the invention or a polynucleotide according to the second aspect of the invention to said cells.

An angiogenic taxic response in cultured endothelial cells involves production of sites of attachment between cells mediated by club-like projections and orientation of cells into pre-angiogenic tubes. It may be assessed visually using a microscope.

The methods of the invention may be practised in vitro or in vivo. Where practised in vivo, the methods of the invention may be used in methods of treatment of animals or humans.

According to a ninth aspect of the present invention there is provided a method of promoting angiogenesis comprising the step of administering a peptide according to the first aspect of the invention or a polynucleotide according to the second aspect of the invention at a therapeutically effective amount to a patient in need thereof.

The promotion of angiogenesis may be useful in a number of clinical conditions. For example, the pro-angiogenic peptide(s) of the invention may be used to promote angiogenesis of collateral vasculature in myocardial tissue during or following ischaemic disease, myocardial infarction or following coronary bypass surgery. Other diseases or conditions which may be treated by the provision of the peptide(s) of the invention include vascular disease and/or ischaemic disease causing pathology of the peripheral or central nervous system. Such conditions/diseases may include cerebrovascular accidents, e.g. caused by clot occlusions or by rupture of aneurysms, or general/localised ischaemia causing neuronal death or peripheral functional impairment such as in motor or sensory functions or speech impairment. Thus, in one embodiment, the peptides, methods and uses of the invention are for the treatment of cerebrovascular accidents. In another embodiment, the peptides, methods and uses of the invention are for use in the treatment of ischaemic disease, which may be general or localised.

Furthermore, the pro-angiogenic properties of the peptide(s) of the invention may be used in the promotion of tissue repair, for example, wound healing. Accordingly, in a seventh aspect of the invention there is provided the use of a peptide of the invention in promoting tissue repair and/or the treatment of a wound.

According to a tenth aspect of the present invention there is provided a method of promoting tissue repair, said method comprising the step of administering a peptide according to the first aspect of the invention or a polynucleotide according to the second aspect of the invention at a therapeutically effective amount to a patient in need thereof.

The peptide(s) and methods of the invention may be used in the repair of any suitable tissue in need thereof. For example, the peptide(s) may be used in the repair of any damaged tissue or the healing of any wound where vascular angiogenesis and/or revascularisation is desired. For example, in one embodiment, wounds which the peptide(s) and methods of the invention may be used to treat include ulcers, such as dermal ulcers, for example pressure sores, venous ulcers, and diabetic ulcers. In another embodiment, the methods and peptide(s) may be used to treat tissue trauma. In one embodiment, the tissue trauma is a wound such as a laceration. In another embodiment, the tissue trauma which the present invention may be used to treat is a burn. The peptides and methods may be particularly useful in applications where transplanted tissues, for example, skin grafts, are employed in the repair of such wounds.

In vascular graft surgery, the peptides and methods of the invention may be used to promote endothelialization. Where vascular grafts using either transplanted or synthetic material are used the peptides may be applied to the surface of the graft to promote the growth of vascular smooth muscle and adventitial cells in conjunction with endothelial cells. Furthermore, where materials, natural or synthetic, are to be transplanted into the body, the peptides of the invention may be used to coat the materials to reduce and/or minimize rejection of the transplanted material and to stimulate vascularization of the transplanted materials.

Thus in an eleventh aspect, the invention provides a method of treating or preventing transplant rejection in a subject, said method comprising the step of administration of a peptide according to the first aspect of the invention or a polynucleotide according to the second aspect of the invention to said subject.

Such peptides may also be useful in the repair of vascular damage caused by arteriosclerosis or damage caused by balloon angioplasty. By promoting repair of such tissues, damage may be minimised and re-stenosis may be prevented. Thus in a further embodiment of the invention, there is provided a method of treating vascular damage in a subject, said method comprising the step of administration of a peptide according to the first aspect of the invention or a polynucleotide according to the second aspect of the invention to said subject Further, more generally, the peptides of the invention also exhibit potency in effecting cell growth; for example of cells located on the surface of a body or internally. In particular the peptide of the invention eg. QUB 698.8, may be used to promote the growth of dermal cells.

Thus, the invention may also be used to treat conditions such as burns. This property of the peptides of the invention may also be used in the promotion of graft revascularisation and in the promotion of healing post-operatively, for example after cosmetic surgery.

According to a twelfth aspect of the invention, there is provided a pharmaceutical composition comprising a peptide according to the first aspect of the invention or a polynucleotide according to the second aspect of the invention, and a pharmaceutically acceptable carrier or excipient.

Furthermore, in a thirteenth aspect, there is provided a peptide according to the first aspect of the invention or a polynucleotide according to the second aspect of the invention for use in medicine.

A fourteenth aspect of the invention provides a peptide according to the first aspect of the invention or a polynucleotide according to the second aspect of the invention for use in the treatment of a cardiovascular disease.

A fifteenth aspect of the invention provides a peptide according to the first aspect of the invention or a polynucleotide according to the second aspect of the invention for use in the treatment of a wound or in tissue repair.

A sixteenth aspect of the invention provides a peptide according to the first aspect of the invention or a polynucleotide according to the second aspect of the invention for use in preventing or inhibiting graft or transplant rejection.

A seventeenth aspect of the invention provides according to the first aspect of the invention or a polynucleotide according to the second aspect of the invention in the preparation of a medicament for the treatment of cardiovascular disease.

An eighteenth aspect of the invention provides the use of a peptide according to the first aspect of the invention or a polynucleotide according to the second aspect of the invention in the preparation of a medicament for the treatment of a wound or for tissue repair.

A nineteenth aspect of the invention provides the use of a peptide according to the first aspect of the invention or a polynucleotide according to the second aspect of the invention in the preparation of a medicament for the treatment of graft or transplant rejection.

A twentieth aspect of the present invention is a wound dressing comprising a peptide of the first aspect of the invention or a polynucleotide according to the second aspect of the invention.

Preferred features of each aspect of the invention are as for each of the other aspects *mutatis mutandis*.

DETAILED DESCRIPTION

Peptides of and for use in the present invention include QUB 698.8 (SEQ ID NO: 2), derivatives and fragments thereof, in particular the derivatives and fragments described above. Herein, the term derivative is used interchangeably with analogue.

In one embodiment, a "fragment" or derivative of QUB 698.8 or for use in the present invention retains the ability of QUB 698.8 to relax arterial smooth muscle with an EC50 less than the EC50 of its constrictory effect on ileal muscle.

In another embodiment, the fragment or derivative of QUB 698.8 retains the ability to promote angiogenesis. Such ability may be assessed using any known technique, for example using an endothelial cell angiogenic tubule formulation assay, an endothelial cell wound scrape essay or an MTT assay, as for example as described in the Examples.

In one embodiment the fragments or derivatives of the invention retain both the arterial smooth muscle dilatory ability and pro-angiogenic ability as defined above.

Other derivatives of the QUB 698.8 peptides of and for use in the invention include multimeric or fusion peptides including QUB 698.8 peptides, analogue or fragments of the invention, and prodrugs including such sequences, the peptide linked to a coupling partner, e.g. an effector molecule, a label, a drug, a toxin and/or a carrier or transport molecule. Techniques for coupling the peptides of the invention to both peptidyl and non-peptidyl coupling partners are well known in the art.

Derivatives of and for use in the present invention further include reverse- or retro-analogues of QUB 698.8 peptides or their synthetic derivatives. See, for example, EP 0497 366, U.S. Pat. No. 5,519,115, and Merrifield et al., 1995, PNAS, 92:3449-53, the disclosures of which are herein incorporated by reference. As described in EP 0497 366, reverse peptides are produced by reversing the amino acid sequence of a naturally occurring or synthetic peptide. Such reverse-peptides retain the same general three-dimensional structure (e.g., alpha-helix) as the parent peptide except for the conformation around internal protease-sensitive sites and the characteristics of the N- and C-termini. Reverse peptides are purported not only to retain the biological activity of the non-reversed "normal" peptide but may possess enhanced properties, including increased biological activity. (See Iwahori et al., 1997, Biol. Pharm. Bull. 20: 267-70). Derivatives of and for use in the present invention may therefore comprise reverse peptides of natural and synthetic QUB 698.8 peptides.

Indeed, such reverse QUB 698.8 peptides and derivatives and fragments thereof constitute a further independent aspect of the present invention. Preferably such reverse QUB 698.8 peptides retain biological activity such as the ability to induce pro-angiogenic responses within cells and tissues and/or the ability to selectively relax arterial smooth muscle.

In one embodiment, a reverse peptide of the invention has the reverse amino acid sequence of the peptide shown in SEQ ID NO. 2.

Thus, in one embodiment of the invention, the reverse peptide has the amino acid sequence:

```
Asn-Ile-Lys-Pro-Leu-Asp        (SEQ ID NO: 9)
```

Peptides (including derivatives, reverse peptides and fragments of either), of and for use in the invention, may be generated wholly or partly by chemical synthesis or by expression from nucleic acid. For example, the peptides of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984)).

Multimeric Peptides

As noted above, peptides of the invention may be in the form of multimers. Thus multimers (for example of 2, 3 or more individual QUB 698.8 analogue monomeric units or fragments) are within the scope of the invention.

Such multimers may be used to prepare a monomeric peptide by preparing a multimeric peptide that includes the monomeric unit, and a cleavable site (i.e., an enzymatically cleavable site), and then cleaving the multimer to yield a desired monomer.

The use of multimers can increase the binding affinity for a receptor. Thus, in the present case, the binding affinity of the peptides of the invention to their receptors, could be increased by using multimers of 2-5, for example 2-3 receptor binding moieties.

The multimers can be homomers or heteromers. As used herein, the term homomer, refers to a multimer containing only polypeptides corresponding to the amino acid sequence of SEQ ID NO. 2 or fragments thereof, or other QUB 698.8 derivatives described herein. These homomers may contain pro-angiogenic peptides of the invention having identical or different amino acid sequences. For example, the multimers can include only pro-angiogenic peptides of the invention having an identical amino acid sequence, or can include fragments or derivatives of pro-angiogenic peptides. The multimer can be a homodimer (e.g., containing pro-angiogenic peptides having identical or different amino acid sequences), homotrimer or homotetramer.

As used herein, the term heteromer refers to a multimer containing one or more heterologous polypeptides (i.e., peptides which are not QUB 698.8 peptides, fragments or derivatives thereof) in addition to QUB 698.8 peptides, fragments or derivatives thereof described herein.

The multimers may be the result of hydrophobic, hydrophilic, ionic and/or covalent associations and/or may be indirectly linked by, for example, liposome formation. Thus, in one embodiment, multimers may be formed when the pro-angiogenic peptides of the invention described herein contact one another in solution. In another embodiment, heteromultimers may be formed when pro-angiogenic peptides of the invention and peptides which are not QUB 698.8 peptides, fragments or derivatives thereof contact antibodies to the polypeptides described herein (including antibodies to the heterologous polypeptide sequence in a fusion protein described herein) in solution. In other embodiments, multimers described herein may be formed by covalent associations with and/or between the pro-angiogenic peptides of the invention (and optionally peptides which are not QUB 698.8 peptides, fragments or derivatives thereof) described herein.

Such covalent associations can involve one or more amino acid residues contained in the QUB 698.8 sequence (e.g., that recited in SEQ ID NO. 2). In one embodiment, the covalent associations are the consequence of chemical or recombinant manipulation. Alternatively, such covalent associations can involve one or more amino acid residues contained in the heterologous polypeptide sequence in a QUB 698.8 fusion protein. In one example, covalent associations are between the heterologous sequence contained in a fusion protein described herein (see, for example, U.S. Pat. No. 5,478,925). In a specific example, the covalent associations are between the heterologous sequence contained in a QUB 698.8-Fc fusion protein described herein. In another specific example, covalent associations of fusion proteins described herein are between heterologous polypeptide sequence from another protein that is capable of forming covalently associated multimers, for example, oseteoprotegerin (see, for example WO 98/49305). In another embodiment, two or more polypeptides described herein are joined through peptide linkers. Examples include those peptide linkers described in U.S. Pat. No. 5,073,627. Proteins comprising multiple QUB 698.8 peptides separated by peptide linkers can be produced using conventional recombinant DNA technology.

Multimers may also be prepared by fusing the pro-angiogenic peptides of the invention to a leucine zipper or isoleucine zipper polypeptide sequence. Among the known leucine zippers are naturally occurring peptides and derivatives thereof that dimerize or trimerize. Examples of leucine zipper domains suitable for producing soluble multimeric proteins described herein are those described in WO 94/10308. Recombinant fusion proteins comprising a polypeptide described herein fused to a polypeptide sequence that dimerizes or trimerizes in solution can be expressed in suitable host cells, and the resulting soluble multimeric fusion protein can be recovered from the culture supernatant using techniques known in the art.

The multimers may also be generated using chemical techniques known in the art. For example, polypeptides desired to be contained in the multimers described herein may be chemically cross-linked using linker molecules and linker molecule length optimization techniques known in the art (see, for example, U.S. Pat. No. 5,478,925). Additionally, the multimers can be generated using techniques known in the art to form one or more inter-molecule cross-links between the cysteine residues located within the sequence of the polypeptides desired to be contained in the multimer (see, for example, U.S. Pat. No. 5,478,925). Further, polypeptides described herein may be routinely modified by the addition of cysteine to the N-terminus or C-terminus or biotin to a suitable amino group either at the N-terminus or the side chain of a Lys residue of a peptide of the invention, for example at Lys-4 of SEQ ID NO: 2. Techniques known in the art may be applied to generate multimers containing one or more of these modified polypeptides (see, for example, U.S. Pat. No. 5,478,925). Additionally, techniques known in the art can be used to prepare liposomes containing two or more peptides of the invention desired to be contained in the multimer (see, for example, U.S. Pat. No. 5,478,925).

Alternatively, those multimers including only naturally-occurring amino acids can be formed using genetic engineering techniques known in the art. Alternatively, those that include post-translational or other modifications can be prepared by a combination of recombinant techniques and chemical modifications. In one embodiment, the pro-angiogenic peptides of the invention are produced recombinantly using fusion protein technology described herein or otherwise known in the art (see, for example, U.S. Pat. No. 5,478,925, which is herein incorporated by reference in its entirety). For example, polynucleotides coding for a homodimer described herein can be generated by ligating a polynucleotide sequence encoding a pro-angiogenic peptide of the invention described herein to sequence encoding a linker polypeptide and then further to a synthetic polynucleotide encoding the translated product of the polypeptide in the reverse orientation from the original C-terminus to the N-terminus (lacking the leader sequence) (see, for example, U.S. Pat. No. 5,478,925). The recombinant techniques described herein or otherwise known in the art can be applied to generate recombinant pro-angiogenic peptides of the invention that contain a transmembrane domain (or hydrophobic or signal peptide) and that can be incorporated by membrane reconstitution techniques into liposomes (see, for example, U.S. Pat. No. 5,478,925).

Pro-Drugs

The peptides described herein are intended, at least in some embodiments, to be administered to a human or other mammal for medical treatment. Peptides are typically administered parenterally, and may be readily metabolized by plasma proteases. Oral administration, which is perhaps the most attractive route of administration, may be even more problematic. In the stomach, acid degrades and enzymes break down the peptides. Those peptides that survive to enter the intestine intact are subjected to additional proteolysis as they are continuously barraged by a variety of enzymes, including gastric and pancreatic enzymes, exo- and endopeptidases, and brush border peptidases. As a result, passage of peptides from the lumen of the intestine into the bloodstream can be severely limited. However, various prodrugs have been developed that enable parenteral and oral administration of therapeutic peptides.

Peptides can be conjugated to various moieties, such as polymeric moieties, to modify the physiochemical properties of the peptide drugs, for example, to increase resistance to acidic and enzymatic degradation and to enhance penetration of such drugs across mucosal membranes. For example, Abuchowski and Davis have described various methods for derivatizating enzymes to provide water-soluble, non-immunogenic, in vivo stabilized products ("Soluble polymers-Enzyme adducts," Enzymes as Drugs, Eds. Holcenberg and Roberts, J. Wiley and Sons, New York, N.Y. (1981)). Abuchowski and Davis discuss various ways of conjugating enzymes with polymeric materials, such as dextrans, polyvinyl pyrrolidones, glycopeptides, polyethylene glycol and polyamino acids. The resulting conjugated polypeptides retain their biological activities and solubility in water for parenteral applications. U.S. Pat. No. 4,179,337 teaches coupling peptides to polyethylene glycol or polypropylene glycol having a molecular weight of 500 to 20,000 Daltons to provide a physiologically active non-immunogenic water soluble polypeptide composition. The polyethylene glycol or polypropylene glycol protects the polypeptide from loss of activity and the composition can be injected into the mammalian circulatory system with substantially no immunogenic response.

U.S. Pat. No. 5,681,811, U.S. Pat. No. 5,438,040 and U.S. Pat. No. 5,359,030 disclose stabilized, conjugated polypeptide complexes including a therapeutic agent coupled to an oligomer that includes lipophilic and hydrophilic moieties. Garmen, et al. describe a protein-PEG prodrug (Garman, A. J., and Kalindjian, S. B., *FEBS Lett.*, 1987, 223, 361-365). A prodrug can be prepared using this chemistry, by first preparing a maleic anhydride reagent from polydispersed MPEG5000 and then conjugating this reagent to the peptides disclosed herein. The reaction of amino acids with maleic anhydrides is well known. The hydrolysis of the maleylamide bond to reform the amine-containing drug is aided by the presence of the neighboring free carboxyl group and the geometry of attack set up by the double bond. The peptides can be released (by hydrolysis of the prodrugs) under physiological conditions.

The peptides can also be coupled to polymers, such as polydispersed PEG, via a degradable linkage, for example, the degradable linkage shown (with respect to pegylated interferon α-2b) in Roberts, M. J., et al., *Adv. Drug Delivery Rev.*, 2002, 54, 459-476.

The peptides can also be linked to polymers such as PEG using 1, 6 or 1,4 benzyl elimination (BE) strategies (see, for example, Lee, S., et al., *Bioconjugate Chem.*, (2001), 12, 163-169; Greenwald, R. B., et al., U.S. Pat. No. 6,180,095, 2001; Greenwald, R. B., et al., J. Med. Chem., 1999, 42, 3657-3667.); the use of trimethyl lock lactonization (TML) (Greenwald, R. B., et al., J. Med. Chem., 2000, 43, 475-487); the coupling of PEG carboxylic acid to a hydroxy-terminated carboxylic acid linker (Roberts, M. J., J. Pharm. Sci., 1998, 87(11), 1440-1445), and PEG prodrugs involving families of MPEG phenyl ethers and MPEG benzamides linked to an amine-containing drug via an aryl carbamate (Roberts, M. J., et al., Adv. Drug Delivery Rev., 2002, 54, 459-476), including a prodrug structure involving a meta relationship between the carbamate and the PEG amide or ether (U.S. Pat. No. 6,413,507); and prodrugs involving a reduction mechanism as opposed to a hydrolysis mechanism (Zalipsky, S., et al., Bioconjugate Chem., 1999, 10(5), 703-707).

Some approaches involve using enzyme inhibitors to slow the rate of degradation of proteins and peptides in the gastrointestinal tract; manipulating pH to inactivate local digestive enzymes; using permeation enhancers to improve the absorption of peptides by increasing their paracellular and transcellular transports; using nanoparticles as particulate carriers to facilitate intact absorption by the intestinal epithelium, especially, Peyer's patches, and to increase resistance to enzyme degradation; liquid emulsions to protect the drug from chemical and enzymatic breakdown in the intestinal lumen; and micelle formulations for poorly water-solubulized drugs.

In some cases, the peptides can be provided in a suitable capsule or tablet with an enteric coating, so that the peptide is not released in the stomach. Alternatively, or additionally, the peptide can be provided as a prodrug. In one embodiment, the peptides are present in these drug delivery devices as prodrugs.

Free amino, hydroxyl, or carboxylic acid groups of the peptides can be used to convert the peptides into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of various polymers, for example, polyalkylene glycols such as polyethylene glycol. Prodrugs also include compounds wherein carbonates, carbamates, amides and alkyl esters are covalently bonded to the above peptides through the C-terminal carboxylic acids.

Prodrugs comprising the peptides of the invention or prodrugs from which peptides of the invention (including analogues and fragments) are released or are releasable are considered to be derivatives of the invention.

Isotopically-labelled peptides or peptide prodrugs are also encompassed by the invention. Such peptides or peptide prodrugs are identical to the peptides or peptide prodrugs of the invention, but for the fact that one or more atoms are replaced by an atom having an atomic mass or mass number different from the atomic mass or mass number usually found in nature. Examples of isotopes that can be incorporated into peptides or pro-drugs of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, and $^{35}$S, respectively. Peptides of the present invention, prodrugs thereof, and/or the prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled peptides and prodrugs thereof can generally be prepared by carrying out readily known procedures, including substituting a readily available isotopically-labeled reagent for a non-isotopically-labeled reagent, e.g., a labeled amino acid.

Peptidomimetics

The present invention further encompasses mimetic peptides of QUB698.8 which can be used as therapeutic peptides. Mimetic QUB 698.8 peptides are short peptides which mimic the biological activity of QUB 698.8. Such mimetic peptides can be obtained from methods known in the art such as, but not limited to, phage display or combinatorial chemistry. For example, the method disclosed by Wrighton, et al., *Science* 273:458-463 (1996) can be used to generate mimetic QUB 698.8 peptides. Thus, in one embodiment of the invention, the term derivative encompasses such mimetic QUB 698.8 peptides.

Nucleic Acid

Peptides of and for use in the present invention may be produced by use of nucleic acid in an expression system.

Accordingly the present invention also provides an isolated polynucleotide which encodes a peptide of the first aspect of the invention.

A polynucleotide according to the invention may be provided as an isolate, in isolated and/or purified form, or free or substantially free of material with which it is naturally associated, such as free or substantially free of nucleic acid flanking the gene in the toad genome, except possibly one or more regulatory sequence(s) for expression. Nucleic acid may be wholly or partially synthetic and may include genomic DNA, cDNA or RNA.

Nucleic acid sequences encoding a peptide in accordance with the present invention can be readily prepared by the skilled person using the information and references contained herein and techniques known in the art.

Modifications to the sequences can be made, e.g. using site directed mutagenesis, to lead to the expression of modified peptide or to take account of codon preference in the host cells used to express the nucleic acid.

In one embodiment, the nucleic acid comprises the nucleic acid sequence:

-GATTTGCCTAAGATCAAC-. (SEQ ID NO: 10)

However, any polynucleotide which encodes a peptide of the first aspect of the invention is also encompassed by the invention. For example, by virtue of the degeneracy of the genetic code, polynucleotides, which encode the QUB698.8 peptide having amino acid sequence SEQ ID NO: 2, but which have a nucleic acid sequence which differs from SEQ ID NO: 10 may be used.

However, for the avoidance of any doubt, in the context of the present invention, a polynucleotide which encodes maximakinin, i.e. the amino acid sequence having Sequence ID No: 1, is not encompassed by polynucleotides of the present invention.

Polynucleotides of and for use in the present invention may comprise DNA or RNA whose sequences reflect the degeneracy of the genetic code and whose base composition would reflect nucleic acid type. These may be produced recombinantly, synthetically, or by any means available to those in the art, including cloning using standard techniques. The polynucleotide may be inserted into any appropriate vector. A further aspect of the invention is such a vector comprising a nucleic acid of the invention. Any suitable vector may be used in the invention. For example, the vector may be a virus (e.g. vaccinia virus, adenovirus, etc.), a plasmid, or cosmid DNA a baculovirus; a yeast vector, a phage, or a chromosome, for example an artificial chromosome.

The nucleic acid may be operably linked to a control sequence which is capable of providing expression of the nucleic acid in a host cell. Suitable host cells for use in the invention may be prokaryotic or eukaryotic and include bacteria, yeast, insect cells and mammalian cells. Mammalian cell lines which may be used include Chinese hamster ovary cells, baby hamster kidney cells, NSO mouse melanoma cells, monkey and human cell lines and derivatives thereof and many others.

A host cell strain that modulates the expression of, modifies, and/or specifically processes the gene product may be used. Such processing may involve glycosylation, ubiquitination, disulfide bond formation and general post-translational modification. Accordingly, the present invention also provides a host cell, which comprises one or more nucleic acids or vectors of the invention.

Also encompassed by the invention is a method of producing a pro-angiogenic peptide of the invention, the method comprising culturing a host cell comprising a polynuceotide of the invention under conditions in which expression of the peptide from the polynucleotide occurs and, optionally, isolating and/or purifying the peptide.

For further details relating to known techniques and protocols for manipulation of nucleic acid, for example, in preparation of nucleic acid constructs, mutagenesis, sequencing, introduction of DNA into cells and gene expression, and analysis of proteins, see, for example, Current Protocols in Molecular Biology, 5th ed., Ausubel et al, eds., John Wiley & sons, 2005 and, Molecular Cloning: a Laboratory Manual: 3$^{rd}$ edition Sambrook et al., Cold Spring Harbor Laboratory Press, 2001.

Administration

Peptides of and for use in the present invention may be administered alone but will preferably be administered as a pharmaceutical composition, which will generally comprise a suitable pharmaceutical excipient, diluent or carrier selected depending on the intended route of administration.

The peptides may be administered to a patient in need of treatment via any suitable route. Some suitable routes of administration include (but are not limited to) oral, rectal, nasal, topical (including buccal and sublingual), vaginal or parenteral (including subcutaneous, intramuscular, intravenous, intradermal, intrathecal and epidural) administration.

For intravenous, injection, or injection at a site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1): 547-556, 1985), poly (2-hydroxyethyl-methacrylate) or ethylene vinyl acetate (Langer et al, J. Biomed. Mater. Res. 15: 167-277, 1981, and Langer, Chem. Tech. 12:98-105, 1982). Liposomes containing the polypeptides are prepared by well-known methods: DE 3,218,121A; Epstein et al, PNAS USA, 82: 3688-3692, 1985; Hwang et al, PNAS USA, 77: 4030-4034, 1980; EP-A-0052522; E-A-0036676; EP-A-0088046; EP-A-0143949; EP-A-0142541; JP-A-83-11808; U.S. Pat. No. 4,485,045 and U.S. Pat. No. 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

The peptides and polynucleotides of the invention may be provided in a wound dressing. Any suitable wound dressing may be used to deliver such peptides or polynucleotides. As will be well known to the skilled person, many types of wound dressings are conventionally known and may be used with the peptides or polynucleotides of the invention. These may include but are not limited to hydrocolloid-based wound dressings, hydrogel-based wound dressings, alginate-based wound dressings, foam-based dressings, or anti-microbial dressings.

Hydrocolloid-based dressings generally comprise sodium carboxymethylcellulose, gelatine, pectin, elastomers, and adhesives bonded to a carrier of semi permeable film or a foam sheet to produce a flat, occlusive, adhesive dressing. The dressing forms a gel on the wound surface, thus promoting moist wound healing. Hydrocolloid fibre may be provided as a hydrofibre dressing, from which fibres are converted from dry dressing to soft coherent gel sheet on contact with exudate.

Hydrogel-based dressing promote wound debridement and consist of a matrix of insoluble polymers with a high water content.

Alginate-based wound dressings comprise calcium alginate, optionally with sodium alginate. On contact with the wound fluid alginates partially dissolve to form a hydrophilic gel. They are very suitable for highly exuding wounds.

Foam dressings may comprise polyurethane or silicone foam.

Anti-microbial dressings may comprise antimicrobial agents, such as silver or iodine containing compounds.

The peptides or polynucleotides of the invention may be used in combination of such dressings and incorporated into such dressings using techniques commonly known in the art.

Examples of the techniques and protocols mentioned above and other techniques and protocols which may be used in accordance with the invention can be found in Remington: The Science and Practice of Pharmacy, 21st edition, Gennaro A R, et al, eds., Lippincott Williams & Wilkins, 2005.

Targeting therapies may be used to deliver the active agent to a target, e.g. arterial smooth muscle, by the use of targeting systems such as antibodies or cell specific ligands.

Dose

The peptides, polynucleotides and/or compositions of the invention are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is ultimately within the responsibility and at the discretion of medical physicians and typically takes account of the disorder to be treated, the condition of the individual patient, the site of delivery, the method of administration and other factors known to practitioners.

Therapeutic Uses

"Treatment" or "therapy" includes any regime that can benefit a human or non-human animal. The treatment may be in respect of an existing condition or may be prophylactic (preventative treatment). Treatment may include curative, alleviation or prophylactic effects.

The peptides and methods of the invention may be used in the treatment of any condition or disorder for which pro-angiogenic molecules and/or vasodilatory molecules may be considered useful. As described above, the peptides of the invention were found to have potent pro-angiogenic actions. Accordingly, the peptides of the invention may be used to treat any condition for which neovascularization ameliorates or cures symptoms. Such conditions may include coronary artery disease, peripheral vascular disease, ischaemic heart disease, ischaemic disease of other organs or organ systems, for example of the peripheral or central nervous system, vascular stenoses, occlusion to peripheral vessels of e.g. limbs, and stroke.

The invention may also be used in the treatment of any condition for which tissue selective bradykinin receptor agonists may be useful. As described above, the peptides of the invention were found to have potent vasodilatory actions. Accordingly, the peptides of the invention may be used to treat any condition for which vasodilation ameliorates or cures symptoms. Such conditions may include hypertension, pulmonary hypertension, coronary artery disease, peripheral vascular disease, ischaemic heart disease, ischaemic disease of other organs or organ systems, vascular stenoses, occlusion to peripheral vessels of e.g. limbs, and stroke. Other conditions for which the invention may find used include the treatment of vasospasm, for example, intra- or post-operatively, and erectile dysfunction.

In one embodiment the pro-angiogenic effect of the peptides of the invention may be utilised in the promotion of angiogenesis of collateral vasculature in myocardial tissue during or following ischaemic disease, myocardial infarction or following coronary bypass surgery.

Diseases or conditions which may be treated by the provision of the peptide(s) of the invention include vascular disease and/or ischaemic disease causing pathology of the peripheral or central nervous system. Such diseases may include cerebrovascular accidents caused by clot occlusions or by rupture of aneurysms or general/localised ischaemia causing neuronal death or peripheral functional impairment such as in motor or sensory functions or speech impairment.

As described herein, the peptide(s) of the invention will be useful in tissue repair, for example wound healing, particularly to re-vascularize damaged tissues or stimulate collateral blood flow during ischemia and where new capillary angiogenesis is desired. The peptides may be used in the repair of any damaged tissue or the healing of any wound where vascular angiogenesis and/or revascularisation is desired. The peptide(s) and methods of the invention may thus be used to treat, for example, ulcers, such as dermal ulcers, for example pressure sores, venous ulcers, and diabetic ulcers, lacerations, burns, and other tissue trauma. The peptide(s) and methods may be particularly useful in applications where transplanted tissues, for example, skin grafts, are employed in the repair of such wounds.

In vascular graft surgery the peptide(s) and methods of the invention may be used to promote endothelialization. Where vascular grafts using either transplanted or synthetic material are used the peptide(s) may be applied to the surface of the graft to promote the growth of vascular smooth muscle and adventitial cells in conjunction with endothelial cells. Furthermore, where materials, natural or synthetic are to be transplanted into the body, the peptide(s) of the invention may be used to coat the materials to reduce and/or minimize rejection of the transplanted material and to stimulate vascularization of the transplanted materials. Such agonists may also be useful in the repair of vascular damage caused by arteriosclerosis or damage caused by balloon angioplasty. By promoting repair of such tissues, damage may be minimised and restenosis may be prevented.

Alternatively, the peptides may be used for the promotion or acceleration of both internal and external cell growth. In particular the peptides may be used for the promotion or acceleration of growth of blood vessels, or dermal cells of the peripheral or central nervous system. This may be particularly useful in the promotion of graft revascularisation, for example in the treatment of burns or after cosmetic surgery.

The present invention further extends to methods of gene therapy using nucleic acids encoding peptides of the present invention.

The invention will now be described further in the following non-limiting examples. Reference is made to the accompanying drawings in which:

FIG. 1 shows the relative molar potencies of the QUB 698.8 peptide on isolated smooth muscle preparations; FIG. 1a shows the effect of QUB 698.8 peptide on rat tail artery and FIG. 1b shows the effect of the QUB 698.8 peptide on the small intestine.

FIG. 2a shows the effect of the QUB 698.8 peptide on the migration of Human Microvascular Endothelial Cells (HMEC-1) in the wound scrape assay.

FIG. 2b shows the effect of the QUB 698.8 peptide at a concentration of $1 \times 10^{-8}$M on the time dependent migration of HMEC-1 in the wound assay compared to a non-treatment control.

FIG. 3 illustrates the effect of the QUB 698.8 peptide on the ability of HMEC-1 to form tubules on matrigel matrices.

FIG. 4 illustrates the effect of the QUB 698.8 peptide on the proliferation of HMEC-1 over 72 hours compared to a non-treatment control.

EXAMPLES

Materials and Methods

Acquisition of Skin Secretion.

Four adult specimens of *Bombina maxima* were obtained from a commercial source and housed in a vivarium under a 12 h/12 h light/dark cycle at 22° C. and fed multivitamin-loaded crickets three times per week. Under these conditions, toads have remained in good health in excess of 3 years. Defensive skin secretions were obtained by two methods and under both sets of conditions, secretions were most pronounced from paired paratoid and tibial glands. Firstly, the dorsal surface was moistened with distilled water followed by three periods of transdermal electrical stimulation (5V, 100 Hz, 140 ms pulse width), each of 10 seconds duration (Tyler et al (1992) *J. Pharmacol. Toxicol. Lett.* 28, 199-200). Skin secretions were washed from the dorsal skin with distilled water, snap-frozen in liquid nitrogen and lyophilized. The second and preferred technique involved gently massaging the dorsal skin surface with a latex-gloved finger that was found to be equally effective in terms of dry weight secretion yield. Both techniques caused no harm and minimal stress to the animals.

Discovery of QUB 698.8.

QUB 698.8 was identified in reverse phase HPLC fractions of maximakinin that had been incubated with human saliva for 2 hours. It was generated from its parent peptide, maximakinin, by combined sequential proteolysis by the cocktail of proteases present in saliva.

Smooth Muscle Bioassays (A) Arterial Smooth Muscle:

Male albino Wistar rats (200-350 g) were euthanized by asphyxiation followed by cervical dislocation.

The tail artery was prepared as previously described (Hirst et al (1994) *Br. J. Radiol.* 67, 795-799). Incubation buffer was 95% $O_2$/5% $CO_2$ oxygenated Krebs' solution (NaCl 118 mM, KCl 4.7 mM, $NaHCO_3$ 25 mM, $NaH_2 PO_4$ 1.15 mM, $CaCl_2$ 2.5 mM, $MgCl_2$ 1.1 mM, glucose 5.6 mM). Constriction or dilation of the arterial smooth muscle preparation was detected by an increase or decrease in pressure generated by water column displacement using pressure transducers connected to a MacLab System (AD Instruments Pty Ltd. Australia). Data were displayed graphically on a Macintosh computer. Viability was determined using a range of bolus phenylephrine (5 µM-10 µM) exposures and the endothelial layer of the artery was removed by bubbling with oxygen for 10 s. Absence of the endothelial layer was confirmed by the lack of relaxation in response to a 30 min perfusion of acetylcholine (50 µM) after preconstriction with phenylephrine (10 µM).

(B) Small Intestinal Smooth Muscle:

For intestinal smooth muscle preparations, one cm thick rings of ileum were carefully placed onto the pins of a MacLab force transducer, one pin acting as a stationary fixed point while the second pin was free, permitting application of tension to the smooth muscle. The muscle rings were gradually exposed to 0.1 g increments in resting tension until the spontaneous contractions originated from a resting tension of 0.5 g. The contracting muscle preparations were allowed to stabilise for 25 min before the application of peptides. After perfusion of arterial preparations with 10 μM phenylephrine to obtain constriction plateaux, relative relaxation was recorded following applications of peptides in the range of $1\times10^{-5}$-$1\times10^{-10}$ M. The intestinal smooth muscle ring preparations were exposed to peptide doses as above and relative changes in tension were recorded.

Results

1. Application of QUB 698.8 to a rat tail arterial smooth muscle preparation produced a dose-dependent relaxation. Detailed responses compared to bradykinin and maximakinin are summarized in Table 1—panel A and FIG. 1a. QUB 698.8 was almost equipotent with bradykinin in this bioassay but more potent than maximakinin.
2. Application of QUB 698.8 to a rat ileal smooth muscle ring preparation produced a dose-dependent constriction. Detailed responses compared to bradykinin and maximakinin are summarized in Table 1—panel A and FIG. 1b. QUB 698.8 was less potent than both bradykinin and maximakinin in this bioassay. These combined data show an optimum concentration of QUB 698.8 two orders of magnitude lower for induction of maximal effect in arterial compared to ileal smooth muscle.
3. Selective arterial smooth muscle dilators often have pro-angiogenic properties so QUB 698.8 was subjected to a range of appropriate bioassays to determine spectra of activity.
4. In the human microvessel endothelial cell wound scrape assay, cells are grown on a glass slide to confluence, a standard-sized wound is made with a pipette tip and time taken to repair tear is measured. QUB 698.8 promoted wound closure 42% faster than non-treated controls at an optimum effective concentration of 10 nanomolar (Table 1—panel B and FIGS. 2a and b).
5. Using an in vitro endothelial cell angiogenic tubule formation assay (Matrigel) QUB 698.8 induced 75% more tubules than time-matched controls at an optimum concentration of 1 nanomolar (Table 1—panel B and FIG. 3).
6. Using a standard MTT assay to monitor potential cell proliferative effects, QUB 698.8 caused a 70% increase in endothelial cell number after 24 h when compared to non-treated controls although there were no significant differences after 48 h. (Table 1—panel B and FIG. 4). This may be indicative of a rapid role in cell cycle synchronization.

Taken together, these data are indicative of a potent role for QUB 698.8 in promoting the growth of new blood vessels at concentrations that would render this peptide one of the most potent agents known at present. The results also indicate potency in effecting the growth of other dermal cell types in accelerating wound closure.

QUB 698.8, fragments and derivatives thereof will thus have clinical efficacy in promoting angiogenesis and in wound and tissue repair of both surface and internal tissues.

The mechanism of action by which the peptides of the invention exerts its angiogenic effects may be through binding a receptor or may involve a binding site that is not in the truest sense a receptor.

Without being bound by any one particular theory, it is believed that, due to its total structural dissimilarity to bradykinin receptor ligands, the target for the peptide is not likely to be a bradykinin receptor. It does not apparently work directly through cytoskeletal modifications. This distinguishes its pro-angiogenic effects from C-terminal fragments of maximakinin that do act through bradykinin receptors.

Furthermore, the potent selective vasodilatory effects herein support the peptide's use in applications in which vasodilation is desired.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

TABLE 1A

Physiological Screens

| Name of Screen | Peptide Activity | % Maximum Response | Optimum Concentration | QUB698.8 $EC_{50}$<br>Mx $Ec_{50}$<br>Bk $EC_{50}$ |
|---|---|---|---|---|
| Rat Tail Artery | Relaxant of pre-constricted artery | 25% relaxation<br>30% relaxation<br>32% relaxation | $10^{-7}$ M<br>$10^{-7}$ M<br>$10^{-6}$ M | $7.00 \times 10^{-9}$ M<br>$6.18 \times 10^{-9}$ M<br>$1.18 \times 10^{-8}$ M |
| Rat Ileum | Constriction of spontaneously contracting ileum | 52% Constriction<br>52% Constriction<br>37% Constriction | $10^{-5}$ M<br>$10^{-6}$ M<br>$10^{-6}$ M | $1.44 \times 10^{-6}$ M<br>$5.34 \times 10^{-7}$ M<br>$1.18 \times 10^{-8}$ M |

TABLE 1B

In vitro angiogenic screens

| Name of screen | Peptide effect | Optimum Concentration | $EC_{50}$ | Maximum % Effect | Other information |
|---|---|---|---|---|---|
| Migration wound scrape T = 7 dose response | Potent promoter of wound closure | $10^{-8}$ M | $3.39 \times 10^{-10}$ | 42% Increase in wound closure compared to time matched control | 50% wound closure in T = 3 hrs |

TABLE 1B-continued

| | | In vitro angiogenic screens | | | |
|---|---|---|---|---|---|
| Name of screen | Peptide effect | Optimum Concentration | $EC_{50}$ | Maximum % Effect | Other information |
| Wound scrape total time to closure | Potent stimulator of initial endothelial migration | $10^{-8}$ M | — | — | Complete wound closure in 16 hrs |
| Endothelial cell tubule formation assay | Potent stimulator of endothelial tubule formation | $10^{-9}$ M | $5.26 \times 10^{-11}$ | 75% increase in tubule formation compared to time matched control | |
| Endothelial cell proliferation assay | Potent stimulator of endothelial cell proliferation | $10^{-8}$ M | $6.59 \times 10^{-11}$ | 70% increase in cell number after 24 hrs | No further increase in proliferation observed after 24 hrs |

The invention claimed is:

1. The peptide consisting of the amino acid sequence:

```
Asp-Leu-Pro-Lys-Ile-Asn.      (SEQ ID NO: 2)
```

2. A pharmaceutical composition comprising the peptide according to claim 1 and a pharmaceutically acceptable carrier or excipient.

3. A composition combination comprising a wound dressing containing and the peptide according to claim 1.

* * * * *

UNITED STATES PATENT AND TRADEMARK OFFICE
CERTIFICATE OF CORRECTION

PATENT NO. : 8,217,011 B2
APPLICATION NO. : 12/449950
DATED : July 10, 2012
INVENTOR(S) : Christopher Shaw et al.

It is certified that error appears in the above-identified patent and that said Letters Patent is hereby corrected as shown below:

Column 22, lines 57-58, cancel the text and insert the following:

--3. A composition comprising a wound dressing containing the peptide according to claim 1.--

Signed and Sealed this
Eleventh Day of September, 2012

David J. Kappos
*Director of the United States Patent and Trademark Office*